US011255778B2

(12) United States Patent
Nishizawa et al.

(10) Patent No.: US 11,255,778 B2
(45) Date of Patent: Feb. 22, 2022

(54) SPECTROSCOPIC ANALYSIS APPARATUS, SPECTROSCOPIC ANALYSIS METHOD, STEEL STRIP PRODUCTION METHOD, AND STEEL STRIP QUALITY ASSURANCE METHOD

(71) Applicant: JFE Steel Corporation, Tokyo (JP)

(72) Inventors: Yuji Nishizawa, Tokyo (JP); Shota Tsuji, Tokyo (JP); Kaho Kato, Tokyo (JP)

(73) Assignee: JFE Steel Corporation, Tokyo (JP)

( * ) Notice: Subject to any disclaimer, the term of this patent is extended or adjusted under 35 U.S.C. 154(b) by 60 days.

(21) Appl. No.: 16/962,083

(22) PCT Filed: Dec. 17, 2018

(86) PCT No.: PCT/JP2018/046266
§ 371 (c)(1),
(2) Date: Jul. 14, 2020

(87) PCT Pub. No.: WO2019/142569
PCT Pub. Date: Jul. 25, 2019

(65) Prior Publication Data
US 2020/0393371 A1 Dec. 17, 2020

(30) Foreign Application Priority Data

Jan. 18, 2018 (JP) .............................. JP2018-006528

(51) Int. Cl.
*G01J 3/00* (2006.01)
*G01N 21/3563* (2014.01)
(Continued)

(52) U.S. Cl.
CPC .......... *G01N 21/3563* (2013.01); *G01C 3/02* (2013.01); *G01N 21/21* (2013.01); *G01N 33/202* (2019.01);
(Continued)

(58) Field of Classification Search
CPC .. G01N 21/314; G01N 21/33; G01N 21/3504; G01J 3/10; G01J 3/42
(Continued)

(56) References Cited

U.S. PATENT DOCUMENTS 4,589,776 A * 5/1986 Carver ................... G01N 21/21
250/225
5,835,220 A 11/1998 Kazama et al.
(Continued)

FOREIGN PATENT DOCUMENTS

EP 2557599 A1 2/2013
JP 03108639 A 5/1991
(Continued)

OTHER PUBLICATIONS

Korean Office Action for Korean Application No. 10-2020-7020032, dated Feb. 18, 2021, with Concise Statement of Relevance of Office Action, 5 pages.
(Continued)

*Primary Examiner* — Md M Rahman
(74) *Attorney, Agent, or Firm* — RatnerPrestia

(57) ABSTRACT

A spectroscopic analysis apparatus includes: a light projecting device; a light receiving device; and an output device, wherein the light receiving device includes: a separator configured to separate reflected light into s-polarized light and p-polarized light; a detector for s-polarized light configured to output an electric signal indicating an intensity of the s-polarized light; and a detector for p-polarized light configured to output an electric signal indicating an intensity of the p-polarized light; and the output device is configured to: calculate an absorbance based on a ratio between the intensities of the s-polarized light and the p-polarized light using the electric signals output from the detector for s-polarized light and the detector for p-polarized light; and
(Continued)

calculate either or both of the composition and the composition ratio of the surface of the measurement target object using an intensity of the absorbance at any desired wavenumber.

5 Claims, 10 Drawing Sheets

(51) Int. Cl.
    *G01N 33/202* (2019.01)
    *G01C 3/02* (2006.01)
    *G01N 21/21* (2006.01)

(52) U.S. Cl.
    CPC . *G01N 2201/061* (2013.01); *G01N 2201/063* (2013.01)

(58) Field of Classification Search
    USPC .......................................................... 356/51
    See application file for complete search history.

(56) References Cited

U.S. PATENT DOCUMENTS

| | | | |
|---|---|---|---|
| 5,844,682 | A | 12/1998 | Kiyomoto et al. |
| 9,803,256 | B2 | 10/2017 | Valdez et al. |
| 2016/0231176 | A1* | 8/2016 | Ishitobi ................... G01J 4/04 |
| 2017/0333982 | A1 | 11/2017 | Matsuki et al. |
| 2018/0283849 | A1 | 10/2018 | Fricout et al. |

FOREIGN PATENT DOCUMENTS

| | | | |
|---|---|---|---|
| JP | 07311312 | A | 11/1995 |
| JP | 2002082060 | A | 3/2002 |
| JP | 3637192 | B2 | 4/2005 |
| JP | 2006091001 | A | 4/2006 |
| JP | 2009294059 | A | 12/2009 |
| JP | 2010261915 | A | 11/2010 |
| JP | 2011222735 | A | 11/2011 |
| JP | 2013148568 | A | 8/2013 |
| JP | 5494895 | B2 | 5/2014 |
| JP | 2014208888 | A | 11/2014 |
| KR | 20100138136 | A | 12/2010 |
| WO | 2005083352 | A1 | 9/2005 |
| WO | 2017055895 | A1 | 4/2017 |

OTHER PUBLICATIONS

Russian Office Action with Search Report for Russian Application No. 2020127254/28, dated Feb. 8, 2021, 3 pages (Russian).
International Search Report and Written Opinion for International Application No. PCT/JP2019/046266 dated Mar. 5, 2019, 5 pages.
Japanese Office Action for Japanese Application No. 2019-515388, dated Jul. 28, 2020, with Concise Statement of Relevance of Office Action, 6 pages.

* cited by examiner $y = 0.017x^2 - 0.023x + 0.0009$

SPECTROSCOPIC ANALYSIS APPARATUS, SPECTROSCOPIC ANALYSIS METHOD, STEEL STRIP PRODUCTION METHOD, AND STEEL STRIP QUALITY ASSURANCE METHOD

CROSS REFERENCE TO RELATED APPLICATIONS

This is the U.S. National Phase application of PCT/JP2018/046266 filed Dec. 17, 2018, which claims priority to Japanese Patent Application No. 2018-006528, filed Jan. 18, 2018, the disclosures of these applications being incorporated herein by reference in their entireties for all purposes.

FIELD OF THE INVENTION

The present invention relates to a spectroscopic analysis apparatus, a spectroscopic analysis method, a steel strip production method, and a steel strip quality assurance method that are to be used for analyzing either or both of the composition and the composition ratio of the surface of a measurement target object.

BACKGROUND OF THE INVENTION

Patent Literature 1 describes a method for analyzing the composition of the surface of a measurement target object. Specifically, the method described in Patent Literature 1 measures, while p-polarized light polarized in parallel to an incident plane and s-polarized light polarized perpendicularly to the incident plane are caused to enter the surface of a measurement target object, the intensity ratio between reflection spectra from these beams of light. The method described in Patent Literature 1 then analyzes the composition of the surface of the measurement target object by dividing the measured intensity ratio by the intensity ratio previously measured with respect to a standard sample between the reflection spectra of p-polarized light and s-polarized light.

PATENT LITERATURE

Patent Literature 1: Japanese Patent No. 3637192

SUMMARY OF THE INVENTION

The method described in Patent Literature 1 assumes that the reflectance of s-polarized light at the incident plane is approximately 1 while using a gold mirror as a reference, and refers to table data to find the reflection spectrum intensity of s-polarized light. That is, the method, described in Patent Literature 1, calculates the intensity ratio substantially based on measurement of the reflection spectrum intensity of p-polarized light only. Therefore, the method described in Patent Literature 1 fails to calculate the intensity ratio with high accuracy when the reflection spectrum intensity of s-polarized light is changed by a disturbance. The method consequently fails to analyze the composition of the surface of a measurement target object with high accuracy. Here, examples of the disturbance are (1) a change in reflection intensity from a measurement target object caused by a change of liftoff or surface roughness, (2) a change of an atmosphere in optical path such as $CO_2$ or steam, (3) dirt on the mirror or a fluctuation of intensity of a light source, and (4) vibration or a shape defect of a measurement target object.

A measurement sequence considered applicable for measuring the reflection spectrum intensity of s-polarized light is to repeat alternately measuring the reflection spectrum intensity of s-polarized light and the reflection spectrum intensity of p-polarized light. However, this measurement sequence requires repeating measuring the reflection spectrum intensity of s-polarized light, switching polarizers, measuring the reflection spectrum intensity of p-polarized light, and switching the polarizers. In this measurement sequence, if a measurement target object is moving, it is also a disturbance because measurement on the same position is not possible. Additionally, it is not possible to eliminate a disturbance such as vibration of a measurement target object.

Furthermore, when the number of times of switching polarizers is increased, measurement cycles are limited by process time of switching the polarizers. As a result, an unmeasurable area where passed during the time of switching polarizers is increased.

Aspects of the present invention have been made in consideration of the above inconveniences, and one objective is to provide a spectroscopic analysis apparatus and a spectroscopic analysis method that enable either or both of the composition and the composition ratio of the surface of a measurement target object to be analyzed with high accuracy even when a disturbance is present. Another objective according to aspects of the present invention is to provide a steel strip production method that enables a steel strip having either or both of a desired surface composition and a desired surface composition ratio to be produced with a high yield. Still another objective according to aspects of the present invention is to provide a steel strip quality assurance method that enables a high-quality steel strip to be provided.

To solve the problem and achieve the object, a spectroscopic analysis apparatus according to aspects of the present invention includes: a light projecting unit configured to project infrared light to a measurement target object; a light receiving unit configured to receive, as reflected light, the infrared light reflected by a surface of the measurement target object; and an output unit configured to calculate either or both of a composition and a composition ratio of the surface of the measurement target object using the reflected light received by the light receiving unit, wherein the light receiving unit includes: a separator configured to separate the reflected light into s-polarized light and p-polarized light; a detector for s-polarized light configured to detect s-polarized light obtained through the separation by the separator and output an electric signal indicating an intensity of the s-polarized light to the output unit; and a detector for p-polarized light configured to detect p-polarized light obtained through the separation by the separator and output an electric signal indicating an intensity of the p-polarized light to the output unit; and the output unit is configured to: calculate an absorbance based on a ratio between the intensities of the s-polarized light and the p-polarized light using the electric signals output from the detector for s-polarized light and the detector for p-polarized light; and calculate either or both of the composition and the composition ratio of the surface of the measurement target object using an intensity of the absorbance at any desired wavenumber.

Moreover, the spectroscopic analysis apparatus according to aspects of the present invention further includes a distance measuring unit configured to measure a distance between a position irradiated with the infrared light on the measurement target object and a spectroscopic measurement apparatus, wherein the output unit corrects the absorbance in accordance with values measured by the distance measuring unit.

Moreover, a spectroscopic analysis method according to aspects of the present invention includes: a step of projecting infrared light to a measurement target object; a step of receiving, as reflected light, the infrared light reflected by a surface of the measurement target object; and a step of outputting that calculates either or both of a composition and a composition ratio of the surface of the measurement target object using the reflected light received at the step of receiving, wherein the step of receiving includes: a step of separating the reflected light into s-polarized light and p-polarized light; a step of detecting s-polarized light obtained through the step of separating, and outputting an electric signal that indicates an intensity of the detected s-polarized light; and a step of detecting p-polarized light obtained through the step of separating, and outputting an electric signal that indicates an intensity of the detected p-polarized light; and the step of outputting includes a step of: calculating an absorbance based on a ratio between the intensities of the s-polarized light and the p-polarized light using the electric signals output at the step of detecting s-polarized light and at the step of detecting p-polarized light; and calculating either or both of the composition and the composition ratio of the surface of the measurement target object using an intensity of the absorbance at any desired wavenumber.

Moreover, a steel strip production method according to aspects of the present invention includes: a step of producing a steel strip; and a step of analyzing either or both of a composition and a composition ratio of a surface of the steel strip produced at the step of producing using the spectroscopic analysis method according to aspects of the present invention.

Moreover, a method of assuring steel strip quality according to aspects of the present invention includes: a step of analyzing either or both of a composition and a composition ratio of a surface of a steel strip using the spectroscopic analysis method according to aspects of the present invention; and a step of conducting quality assurance of the steel strip based on an analysis result obtained at the step of analyzing.

The spectroscopic analysis apparatus and the spectroscopic analysis method according to aspects of the present invention enable either or both of the composition and the composition ratio of the surface of a measurement target object to be analyzed with high accuracy even when a disturbance is present. A steel strip production method according to aspects of the present invention enables a steel strip having either or both of a desired surface composition and a desired surface composition ratio to be produced with a high yield. A steel strip quality assurance method according to aspects of the present invention enables a high-quality steel strip to be provided.

DETAILED DESCRIPTION OF EMBODIMENTS OF THE INVENTION

Figure 1:
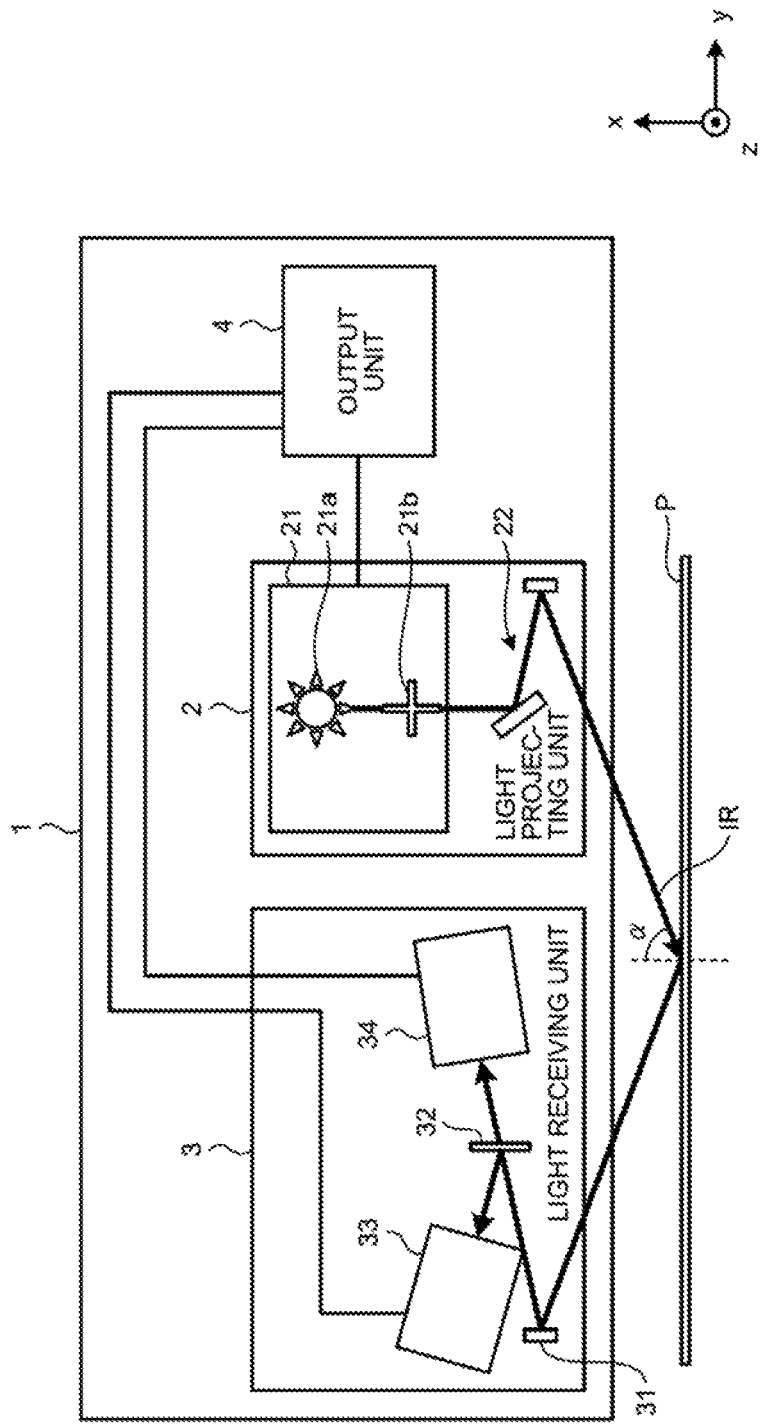
FIG. 1 is a schematic view illustrating the configuration of a spectroscopic analysis apparatus as an embodiment according to aspects of the present invention.

The principle of a spectroscopic analysis method according to aspects of the present invention is described hereinbelow.

When a measurement target object is of a metal material, the irradiated infrared light undergoes a 180° phase change due to the interaction with free electron in the metal. Therefore, when the electric field vector, that is, the polarization direction of the infrared light is perpendicular to an incident plane (p-polarized light), the electric field vector of the incident light and the electric field vector of the reflected light interfere with each other on the incident plane and a standing wave is formed. Consequently, a reflection spectrum contains information of a thin film on the incident plane.

In contrast, when the electric field vector of the infrared light is parallel to the incident plane (s-polarized light), the electric field vectors do not interfere with each other, whereby a reflection spectrum does not contain information of the thin film on the incident plane. Therefore, when the measurement target object is irradiated with p-polarized light, information of the thin film present on the surface of the measurement target object can be specifically acquired. Disturbances during measurement occur in the same manners regardless of whether the incident light is s-polarized light or p-polarized light. Thus, in accordance with aspects of the present invention, s-polarized light and p-polarized light are measured at the same time, and a ratio therebetween is taken, so that impacts of disturbance are eliminated.

Specifically, the ratio (Absorption) between the reflectance of p-polarized light (Reflectance (P)) and the reflectance of s-polarized light (Reflectance (S)) as presented by Equation (1) given below is calculated, whereby a reflection spectrum that contains information on a thin film can be acquired.

$$\text{Absorption (\%)} = \text{Reflectance }(P)/\text{Reflectance }(S) \qquad (1)$$

In actual measurement, however, the reflection spectrum contains noise due to disturbances. With the noise taken into consideration, the s-polarized light reflectance (Reflectance (S)) and the p-polarized light reflectance (Reflectance (P)) are expressed as Equations (2) and (3) given below.

$$\text{Reflectance }(S) = \text{Reflectance }(S) \times \text{noise} \qquad (2)$$

$$\text{Reflectance }(P) = \text{Reflectance }(P) \times \text{noise} \qquad (3)$$

With the noise (noise) taken into consideration, the ratio (Absorption) between the s-polarized light reflectance (Reflectance (S)) and the p-polarized light reflectance (Reflectance (P)) is expressed as Equation (4) given below. As is apparent from Equation (4), it can be found that effects of disturbances can be eliminated by acquiring signals corresponding to the s-polarized light reflectance (Reflectance (S)) and the p-polarized light reflectance (Reflectance (P)) and taking the ratio (Absorption) of them.

$$\text{Absorption} = \text{Reflectance }(P) \times \text{noise}/\text{Reflectance }(S) \times \text{noise} = \text{Reflectance }(P)/\text{Reflectance }(S) \qquad (4)$$

The spectroscopic analysis method according to aspects of the present invention thus enables either or both of the composition and the composition ratio of the surface of the measurement target object to be analyzed with high accuracy even when disturbance is present. Additionally, the spectroscopic analysis method according to aspects of the present invention makes it absolutely unnecessary to perform reference measurement using a gold mirror or a metal mirror, which is often used in an ordinary Fourier transform infrared spectroscopy (FTIR) measurement. That is, because the spectroscopic analysis method according to aspects of the present invention enables measurement using only signals corresponding to s-polarized light and p-polarized light that have been reflected by a measurement target object, there is no need to perform corrections using data measured off-line.

The configuration of a spectroscopic analysis apparatus as an embodiment according to aspects of the present invention that is based on the spectroscopic analysis method according to aspects of the present invention is described hereinbelow.

[Configuration]

FIG. 1 is a schematic view illustrating the configuration of a spectroscopic analysis apparatus as an embodiment according to aspects of the present invention. As illustrated in FIG. 1, a spectroscopic analysis apparatus 1 as an embodiment according to aspects of the present invention is an apparatus for analyzing either or both of the composition and composition ratio of the surface of a measurement target object P, and includes a light projecting unit 2, a light receiving unit 3, and an output unit 4 as main components. As the measurement target object P, any material which have a base layer that reflect infrared light and a layer that absorbs infrared light on the top surface, is applicable. Specific examples include a steel strip, which needs to perform whole surface inspection online. In the present specification, an x-direction, a y-direction, and a z-direction are defined as follows: the x-direction is a direction within a horizontal plane across which the spectroscopic analysis apparatus 1 and the surface of the measurement target object P face each other (liftoff-adjustment direction); the y-direction is a direction within a horizontal plane orthogonal to the x-direction, that is parallel to the width direction of the measurement target object P (direction of the width direction of measurement target object); and the z-direction is a direction of measurement target object P conveyed, that is perpendicular to the x-direction and the y-direction (height and horizontal-adjustment direction).

The light projecting unit 2 includes an FTIR unit 21 and an objective mirror 22. The FTIR unit 21 includes a light source 21a and an interferometer 21b. The light source 21a is constructed of a general infrared light source, such as a ceramic heater, that is used in FTIR and irradiates to the interferometer 21b. The interferometer 21b collimates the infrared light from the light source 21a and outputs the collimated infrared light to the objective mirror 22. The objective mirror 22 is constructed of a flat-surface mirror or an off-axis paraboloid, for example, and projects the infrared light output from the interferometer 21b, as infrared light IR, toward the surface of the measurement target object P at a certain projection angle.

The projection angle α of the infrared light IR is desirably 60° or more. As used in the present specification, the projection angle α means an angle formed with the optical path of infrared light IR and a perpendicular of the measurement target object P. A perpendicular projection angle is defined to be 0°, and a projection angle parallel to the surface of the measurement target object P is defined to be 90°. It is generally known that, as the light projection angle α is larger, an interaction length with the measurement target object P is longer, resulting in a higher sensitivity. However, such factors as surface attributes and attributes of a coating present on the surface of the measurement target object P may possibly lower the sensitivity, for example, by worsening impacts of scattering. It is therefore desirable that the light projection angle α is set to an optimal value experimentally obtained.

Additionally, as the light projection angle α is larger, the apparatus inevitably has larger dimensions to keep the distance (liftoff, x-direction distance) between the measurement target object P and the spectroscopic analysis apparatus 1. The optical path of the infrared light IR is consequently longer, which is another inconvenience. As the optical path of the infrared light IR is longer, small positional change causes a larger shift of optical path. This point clearly indicates that stricter installation accuracy of the spectroscopic analysis apparatus 1 is demanded. Still another inconvenience by having a longer optical path of the infrared light IR is that it exacerbates the impact of a change in an ambient atmosphere midway through the optical path. Furthermore, even if an attempt is made to place the measurement target object P closer for reducing the size of the apparatus and facilitating adjustments, the measurement target object P in motion has a risk of making contact with a casing because, for example, the measurement target object P may flutter, have a defective shape, or have a non-stationary part such as a welded point, which restricts how close the measurement target object P can be placed.

While the above-described liftoff may be designed as appropriate in accordance with the amplitude of fluttering of the measurement target object P and restrictions on installation of the apparatus, as the liftoff is larger, the apparatus needs to become larger in size and adjustments of optical path are more difficult. In contrast, when the liftoff is small, the measurement target object P and the spectroscopic analysis apparatus 1 have a risk of making contact with each other due to the fluttering of the measurement target object P or the like. Therefore, the liftoff needs to be determined with consideration of safety. When the measurement target object P is a steel strip on a continuous line, the liftoff needs to be determined with consideration of: a non-stationary part such as a welding point of the steel strip; the shape of the strip; and blanking and piercing in maintenance or other work to be performed by an operator.

The light receiving unit 3 includes an objective mirror 31, a polarized-light separating unit 32, a p-polarized light detecting unit 33, and an s-polarized light detecting unit 34. The objective mirror 31 reflects the reflected light of the infrared light IR from the measurement target object P toward the polarized-light separating unit 32. The polarized-light separating unit 32 is constructed of a polarizing beam splitter. The polarized-light separating unit 32 splits the reflected light from the objective mirror 31 into s-polarized light and p-polarized light and supplies the p-polarized light and the s-polarized light to the p-polarized light detecting unit 33 and the s-polarized light detecting unit 34, respectively.

Each of the p-polarized light detecting unit 33 and the s-polarized light detecting unit 34 is constructed of an infrared detecting element, such as triglycine sulfate (TGS), that is used for FTIR in general. The p-polarized light detecting unit 33 detects the interferogram of p-polarized light obtained through the separation by the polarized-light separating unit 32, converts the intensity of the interferogram of p-polarized light into an electric signal, and outputs the electric signal to the output unit 4. The s-polarized light detecting unit 34 detects the interferogram of s-polarized light obtained through the separation by the polarized-light separating unit 32, converts the intensity of the interferogram of s-polarized light into an electric signal, and outputs the electric signal to the output unit 4.

In this case, the p-polarized light detecting unit 33 and the s-polarized light detecting unit 34 are desirably constructed of individual separate elements. Including individual separate detectors for p-polarized light and s-polarized light makes it possible to simultaneously acquire respective signals corresponding to p-polarized light and s-polarized light. Including individual separate detectors for p-polarized light and s-polarized light also makes it possible to process differences between the two detectors, whereby measurement can be more robust against disturbances such as a change in the atmosphere, a fluctuation of the light source, and a defect in the field of view that occurs midway through the path of the optical system.

Another possible configuration includes a detection unit composed of the polarizers and a single detector, in which measurement is conducted while switching between p-polarized light and s-polarized light by switching or rotating the polarizers, for example. In such a case, however, while one type of polarized light is measured, the other type of polarized light cannot be measured. That is, p-polarized light cannot be measured while s-polarized light is being measured, and vice versa. When a disturbance such as the quick fluctuation of atmosphere occurs during such switching, the disturbance affects the measurement.

In on-line measurement, measurement positions change moment by moment, and measurement positions corresponding to s-polarized light and corresponding to p-polarized light are therefore different. It is therefore impossible to reduce effects of disturbance using the difference between a signal corresponding to s-polarized light and a signal corresponding to p-polarized light. Thus, in on-line measurement, it is needed to include individual separate detectors, separate s-polarized light and p-polarized light through a polarizing beam splitter, and simultaneously measure these separated components of light using the corresponding detectors.

A wire grid polarizer is desirably used as a polarizing beam splitter in the polarized-light separating unit 32. Specifically, in general, there is only a few materials that transmit infrared light, so cannot apply a volume-based beam splitter as in the case of visible light. It is therefore preferable to apply a wire grid polarizer which is used for a polarizer for the infrared region, and separate s-polarized light as transmitted light and p-polarized light as reflected light, for example. Also, the opposite manner of separation is allowed.

When the beam splitter material has low transmittance, light quantity is inevitably low and makes the measurement impossible, or other inconveniences such as the occurrence of a pseudo-peak due to a less S/N ratio are caused. For this reason, the polarizer is desirably made of a material having transmittance of 70% or more in a range of wavenumbers to be measured. Because the mixture of unintended polarized light reduces sensitivity, it is desirable to exceed an extinction ratio, which indicates the mixture ratio of unintended polarized light, of 100 or more.

The material of an optical element used as the polarizing beam splitter may be selected from, for example, barium fluoride ($BaF_2$), thallium bromoiodide (KRS-5), ZnSe, and germanium, as appropriate. In order to increase polarization purity, a polarizer which is orthogonal by 90 degrees to the polarizing beam splitter, may be set in front of a detector on the reflection side. This disposition is because a polarized light component supposed to be transmitted is mixed into the reflected light because of Fresnel reflection at the surface of the polarizer. This mixture results to a lower S/N ratio.

The output unit 4 is constructed of an arithmetic processing unit such as a computer and performs the below-described spectroscopic analysis process on electric signals output from the p-polarized light detecting unit 33 and the s-polarized light detecting unit 34, thereby analyzing either or both of the composition and the composition ratio of the surface of the measurement target object P.

When the spectroscopic analysis apparatus 1 is applied to oxide film evaluation on a continuous production line in a steel sheet production factory, measures to control the environment are desired. Examples of factors that negatively affect the measurement include powder dust, $CO_2$, and steam. When $CO_2$ or steam is present midway through the path, infrared light is absorbed. When powder dust is present, infrared light not only is absorbed by the raw materials of powder dust but also is scattered in such a manner that the light quantity thereof is reduced. Furthermore, exposure of optical components such as a mirror to powder dust or steam deteriorates the mirror and other components of the apparatus. It is therefore desirable to carry out a purge using an inert gas such as dry nitrogen or argon or to employ a tightly sealed structure using an optical window.

Specifically, when measures are designed to prevent the effect of steam or powder dusts without any effects to the optical properties, subjecting the entire optical system to a purge using an inert gas to eliminate powder dust or steam is considered possible. While the arrangement of optical systems and window dimensions that are determined depending on that arrangement may be designed as appropriate in consideration of the ambient atmosphere, blow-in of argon or dry nitrogen gas of a constant pressure is an easily applicable design. An employable structure is one such that a purge gas is blown out from two holes made in a surface that face a measurement target, specifically in parts in which optical path are present. While the diameters of the holes may be determined in accordance with the diameters of the optical path, the holes preferably have, for example, diameters of about 2 cm. The holes that have too large diameters necessitate a higher purge pressure, which means a higher cost for the gas. Additionally, intrusion of powder dust is facilitated, which makes the holes useless. The holes that have too small diameters in contrast interfere with infrared light and are therefore inappropriate.

However, the above configuration makes it necessary to conduct constant purges after the installation, which causes a concern about a running cost of purge gas. Given this concern, a possible approach is to attach a window to the optical path and the other area are sealed off. A window material inserted into a light reception and projection path for infrared light needs to have a high transmittance for the range of wavenumbers to be measured that is 800 to 1400 $cm^{-1}$. The optical system according to the present embodiment includes at least two windows in the light projecting side and the light receiving side. Therefore, the light intensity is remarkably reduced when the windows have low transmittance. For this reason, a material having transmittance of 60% or more, more preferably, 80% or more is selected. Obviously, a material being polarization-independent and having a flat transmission characteristic is desirable. Furthermore, when a window material is used, selection of the material based on the surface hardness is also an important design matter. The material of window having higher hardness is more desirable in order that no scars be left on the window material when cleaning the window material after the powder dust adheres on the window material.

In this spectroscopic analysis apparatus 1, the light projection angle α of the infrared light IR is large, and the detection sensitivity is significantly affected by the small fluctuation of focal point. For this reason, the spectroscopic analysis apparatus 1 desirably includes internally a distance measuring device that measures the distance between a measurement position of the measurement target object P and the spectroscopic analysis apparatus 1 (x-direction distance). As the distance measuring device, a commonly used distance meter may be used while the measurement accuracy is desirably 0.1 mm or less. A measurement range may be determined in accordance with the distance between the distance measuring device and the measurement target object P. As the distance measuring device, a laser range finder or the like is suitable. The distance measuring device can be used to measure the distance between the measurement target object P and the spectroscopic analysis apparatus 1 to utilize the measured distance for adjustment when the apparatus is installed.

Figure 2:
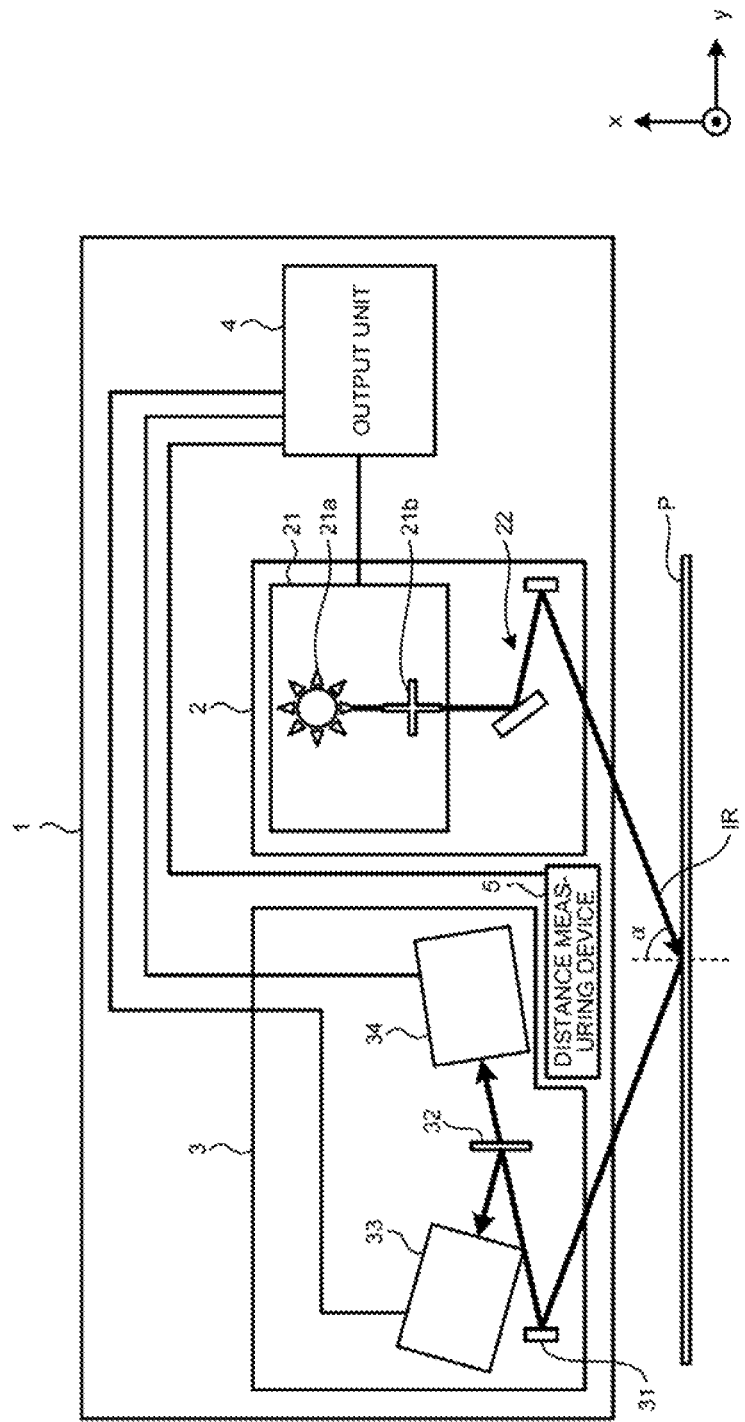
FIG. 2 is a schematic view illustrating the configuration of a modification of the spectroscopic analysis apparatus illustrated in FIG. 1.

An example of the configuration of the apparatus including a distance measuring device is illustrated in FIG. 2. As illustrated in FIG. 2, a distance measuring device 5 is installed in a position such that a measurement position substantially coincides with the focus position of the infrared light IR. Specifically, a distance to the measurement target object P is measured at the measurement position of spectroscopic analysis apparatus 1 with the distance measuring device 5, wherein the distance measuring device 5 is installed so that the optical path height of the infrared light IR (z-direction height) and the installation height of the distance measuring device 5 (z-direction height) can be the same height and that the measurement position of the distance measuring device 5 coincides with the center of the measurement position (focal point position) of the spectroscopic analysis apparatus 1 from the position of the optical path of incidence and reflection of the infrared light IR.

Wavelength of the light projecting unit 2 is infrared. Therefore, a mirror having a long focal length needs to be used in the present optical system, which does not allow intensive light collection. Therefore, the size of IR measurement spot (focal point) is about several millimeters. For this reason, the measurement position of the distance measuring device 5 may be set within the size of this spot. When a laser range finder is used as the distance measuring device 5, a measurement spot is about 1 mm or less in most cases, the distance measuring device 5 may be set near the center of the spot of infrared light.

In addition, a position that provides the highest signal intensity is determined as the focal-point position based on previous sample measurement or the like, and a value then measured by the distance measuring device 5 is recorded previously. When the apparatus is installed in a production line for example, the position of the installation can be determined with reference to the measured value, that is, the focal-point position. It is thus desirable that the distance measuring device 5 is installed in a central part of the spectroscopic analysis apparatus 1 so that the measurement position of the distance measuring device 5 and the measurement position of the spectroscopic analysis apparatus 1 can coincide with each other. The spectroscopic analysis apparatus 1 can have the space for installing the distance measuring device 5 in the central part, because the configuration in which the light projection angle α of the infrared light IR is large. The distance measuring device 5 therefore can be installed without interfering with the optical path of infrared light.

When a laser range finder is used as the distance measuring device 5, it is needed to prevent dust intrusion by installing, on a casing of the spectroscopic analysis apparatus 1, an optical window for the distance measuring device 5. The laser range finder utilizes visible light, a window material, such as glass, that transmits visible light can be used. However, the use of a glass window may cause refraction, whereby a value measured by the laser range finder may be incorrect. It is needed to use a glass window after the accuracy thereof is checked.

As an example, a triangulation-based laser range finder was used as the distance measuring device 5. The laser range finder is installed in such a manner as to coincide with the focal point of infrared light, and the central point of infrared light and the optical path of the laser range finder are set so as to coincide with each other at the liftoff is set to 50 mm, which is a reference value of liftoff. Glass of about 0.8 mm was attached to the laser range finder as a window material to form a sealed-off structure so that intrusion of powder dust from the outside can be prevented. Measurement value of laser range finder was checked before and after the glass was installed and, although an offset of about 1 mm was found, the linearity was substantially maintained. Because the reference value of the liftoff is 50 mm, adjustment for on-line installation was carried out so that the value measured by the laser range finder correspond to the reference value.

Figure 3:
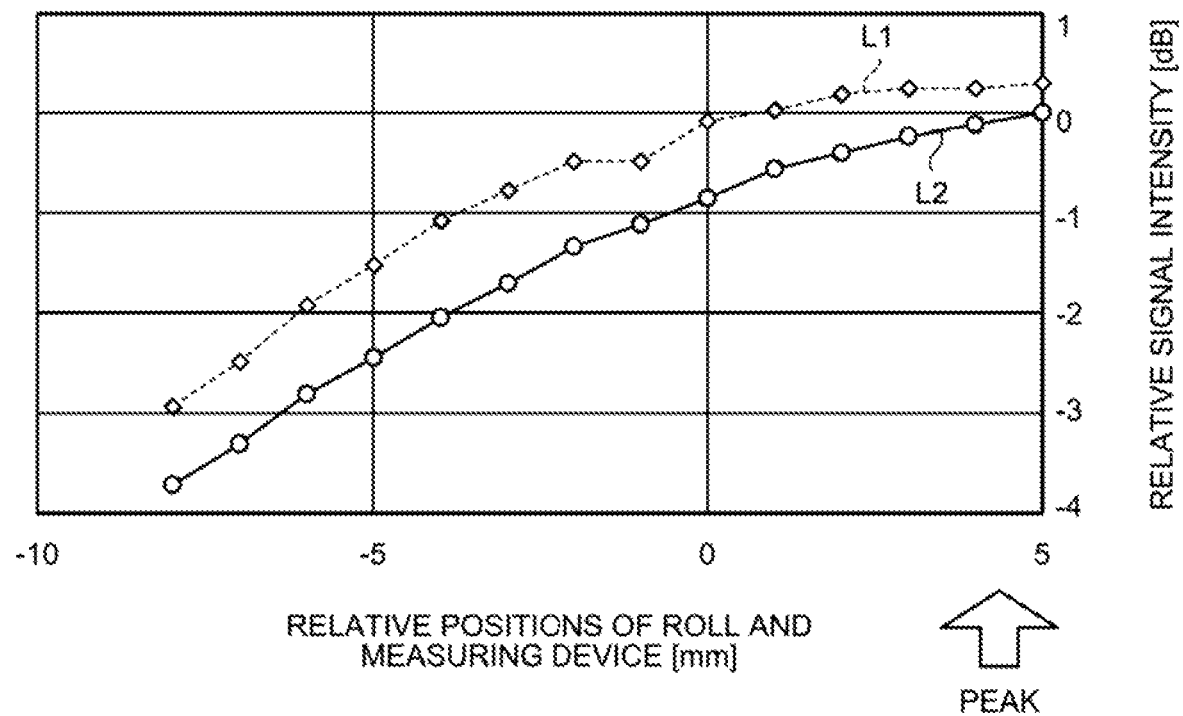
FIG. 3 illustrates changes in signal intensity of p-polarized light and s-polarized light that accompany changes in relative positions of a roll and a distance measuring device.

FIG. 3 illustrates changes in signal intensity of p-polarized light and s-polarized light that accompany changes in relative positions of a roll and a distance measuring device. In FIG. 3, a line L1 represents the signal intensity of p-polarized light and a line L2 represents the signal intensity of s-polarized light. The vertical axis represents a relative signal intensity (dB). The relative signal intensity substantially at the peaks of the line L1 and the line L2 is set to 0 dB, and the measuring scale thereof is in the units of 1 dB. As illustrated in FIG. 3, when the measurement target object P is measured at a roll-wrapping part that is wrapped around a cylindrical conveyance roll that is rotating around a rotation axis extending in the y-axis direction, the signal intensities decrease when the optical path (relative position between the roll and the distance measuring device 5) is shifted from the peak of the roll in the z-direction. More specifically, while the signal intensity is highest at the peak of the roll when the x-direction distance between the measurement target object P and the spectroscopic analysis apparatus 1, the signal intensity decreases farther away from the peak of the roll. In addition to simple decrease of the signal intensity, wavelength dependency is observed in some cases. For this reason, based on the signal intensities, the position of the spectroscopic analysis apparatus 1 in the z-direction needs to be adjusted to a position in the z-direction that faces the peak of the roll.

Figure 4:
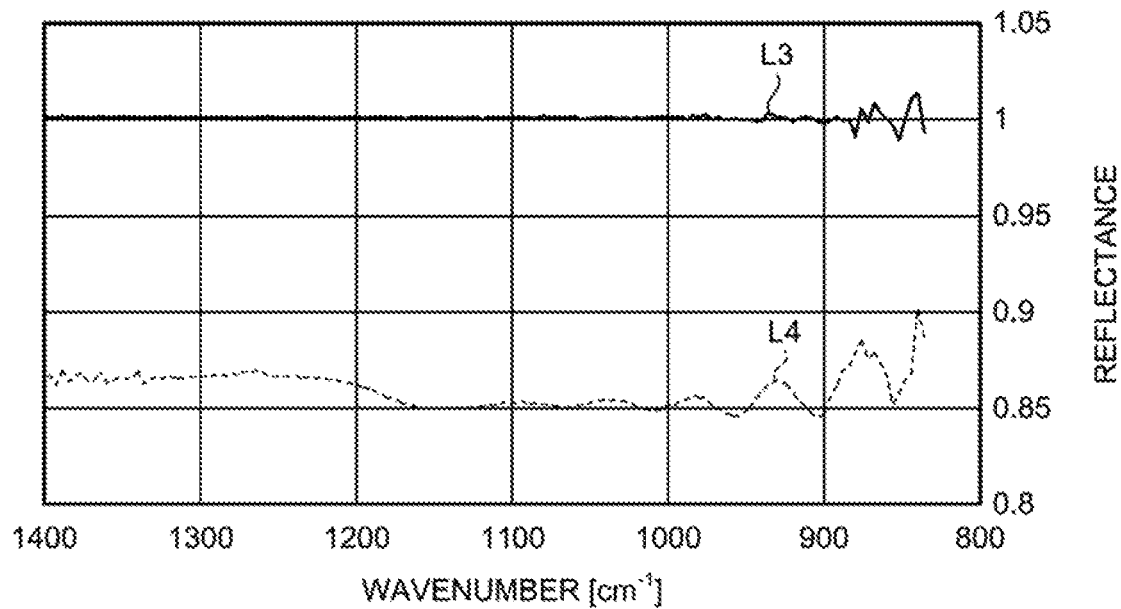
FIG. 4 illustrates an example of change in reflection spectrum of p-polarized light when the focus was intentionally missed.
Figure 5:
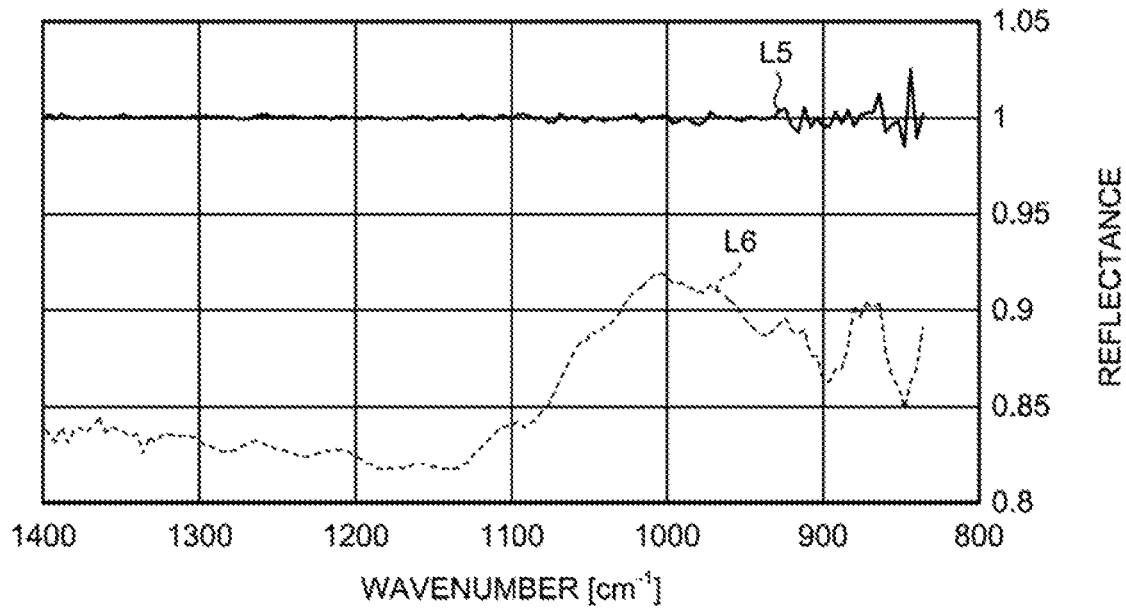
FIG. 5 illustrates an example of change in reflection spectrum of s-polarized light when the focus was intentionally missed.

In contrast, FIG. 4 and FIG. 5 illustrate examples of change in reflection spectra of p-polarized light and s-polarized light when the focus was intentionally missed with a gold mirror used as a reference. FIG. 4 and FIG. 5 illustrate change in reflection spectra when the focus of a flat-surface mirror was intentionally missed 3 mm farther away (in a direction in which the x-direction distance between the spectroscopic analysis apparatus 1 and the measurement target object P increases). While solid lines L3 and L5 represent reflection spectra when the focus was not missed, broken lines L4 and L6 represent reflection spectra when the focus was intentionally missed. As illustrated in FIG. 4 and FIG. 5, it can be found that, when the focus was intentionally missed in the x-direction, no significant change appears in the reflection spectrum of p-polarized light, singular peaks appear in the reflection spectrum of s-polarized light. This is considered to be attributable to factors such as a reduction in light quantity due to dimensional restrictions of parts midway through the optical system as a result of change of the optical path, and fluctuation in detection sensitivity of parts midway through the optical system or of a detection element. Given the above discussion, a positional adjustment between the spectroscopic analysis apparatus 1 and the measurement target object P is an important parameter.

Figure 6:
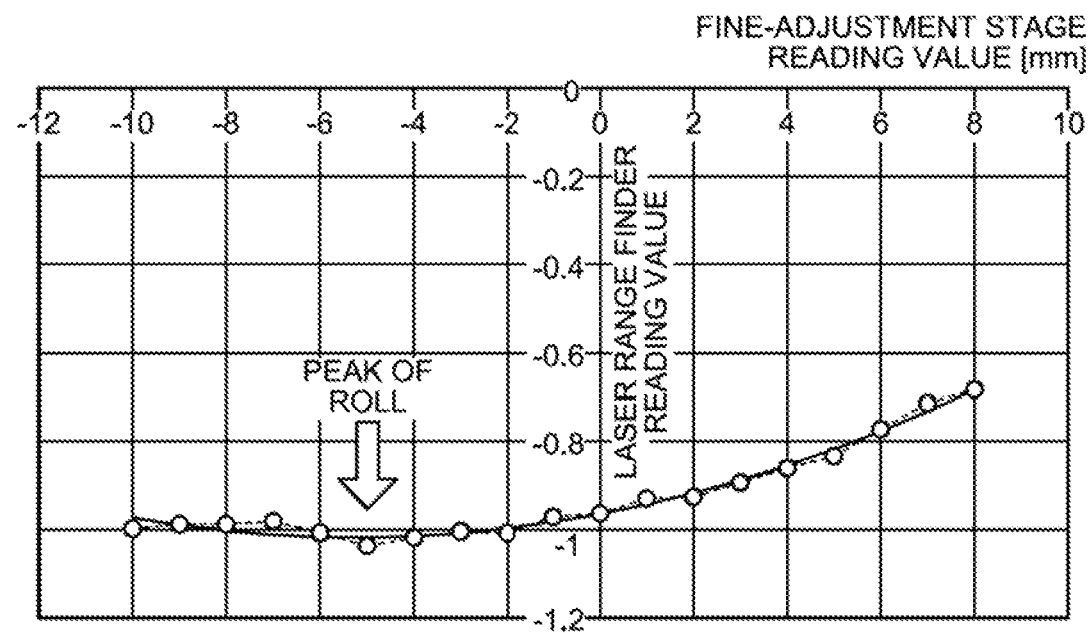
FIG. 6 illustrates an example in which a distance to a measurement target object is measured while a distance measuring device was moved up and down using a fine-adjustment stage.

The peak position of the roll can be detected also from a value measured by the distance measuring device 5. FIG. 6 illustrates an example in which a distance to a measurement target object P in the x-direction was measured while a laser range finder was moved up and down in the z-direction using a fine-adjustment stage. The horizontal axis represents the relative position between the roll and the laser range finder, and the vertical axis represents values measured by the laser range finder. As illustrated in FIG. 6, the peak position of the roll can be found by applying curve approximation to the values measured by the laser range finder and obtaining, using a fitted curve obtained by the curve approximation, a position at which the values measured by the laser range finder have the smallest value.

Measurement at the roll-wrapping part can be considered to be carried out at a measurement position favorable for conducting on-line measurement in consideration of conveying stability of the path line. In contrast, when the measurement position is off from the peak of the roll, the reflection angle of the infrared light IR is changed because the measurement target object P is warped. This results in reduction of the signal intensity. For this reason, it is needed to detect the peak of the roll and adjust the measurement position to the peak of the roll, for which a method for quantitative assessment and identification is needed. Thus, as in FIG. 6, it is confirmed that the peak of the roll can be detected from the values measured by the distance measuring device 5. It is also confirmed that the position of the peak was almost the same position when checked with the alignment beam and when checked with visual observation.

It is desirable, however, that the position of the peak is determined by applying parabolic approximation fitting to several points for which values are measured as distances and then calculating the position of the peak of the roll. This is because an error may occur to reading value of the laser range finder and also because there are small difference in value near the peak of the large diameter roll. Specifically, the position of the peak of the roll can be calculated by measuring the liftoff with respect to at least several points within an arbitrary range (specifically about 20 mm) centering on the peak and applying arc approximation or quadratic-function approximation is applied to a group of those points. In the present apparatus, the optical path is invisible because infrared light are used. For that reason, the effect of enabling installation position adjustment using light of the laser range finder as a guide is produced.

It is desirable that a multi-axis adjustment mechanism be provided for adjustment of the position of the spectroscopic analysis apparatus 1. Representatively, a six-axis adjustment mechanism may be provided. The number of axes can be reduced depending on factors such as the level of installation accuracy needed for an actual apparatus.

Specifically, a three-axis adjustment mechanism may be used for leveling the main body of the spectroscopic analysis apparatus 1 and for angular adjustments with the measurement target object P (adjustments in the z-direction). In angle adjustment between the spectroscopic analysis apparatus 1 and the measurement target object P, precise adjustment is needed. It is also needed to perform not only an adjustment aiming at the peak of the roll but also fine adjustments such as securing that a mounting is horizontal and causing the optical path perpendicular to a measurement point when measurement is performed at the roll-wrapping part. For this reason, it is needed to perform fine adjustments in terms of height and the horizontal degree.

A single-axis adjustment mechanism may be used for positional adjustments in the widthwise direction with the measurement target object P (adjustments in the y-direction). For example, when the distribution in the width direction is measured on-line, the adjustment is needed. The adjustment range may be determined in accordance with the width of a measurement target and the degree of variations in a target on which measurement needs to be performed. A single-axis adjustment mechanism is utilized for tracking the sheet width when there is a need to concentrate the measurement on an edge part in which non-stationarity is more likely to occur.

A two-axis adjustment mechanism may be utilized for a liftoff adjustment and rotation and tilt adjustments (adjustments in the x-direction) between the measurement target object P and the spectroscopic analysis apparatus 1. When the liftoff changes, the position of reflected light changes, which significantly affects the signal intensity. Additionally, when the main body spectroscopic analysis apparatus 1 is installed in a tilted manner, the angle of incidence and the angle of reflection of the infrared light IR deviate, which involves a risk of having the signal intensity significantly reduced. For these reasons, it is desirable that a liftoff adjustment and a tilt adjustment can be performed independently of each other. A two-axis adjustment mechanism can also be utilized for tracking changes in the thickness of measurement target object P.

As an adjustment mechanism, an electric actuator or the like may be used, and an electric actuator that has a needed resolution and a load characteristic that enables the electric actuator to support the weight of the spectroscopic analysis apparatus 1 may be adopted. High accuracy is demanded particularly for adjustment axes in the z-direction and the x-direction, and it is therefore desirable that the adjustment mechanism has a resolution of 0.01 mm or less.

Spectroscopic Analysis Process

Next, with reference to FIG. 7 to FIG. 16, the procedure of a spectroscopic analysis process as an embodiment according to aspects of the present invention is described.

Figure 7:
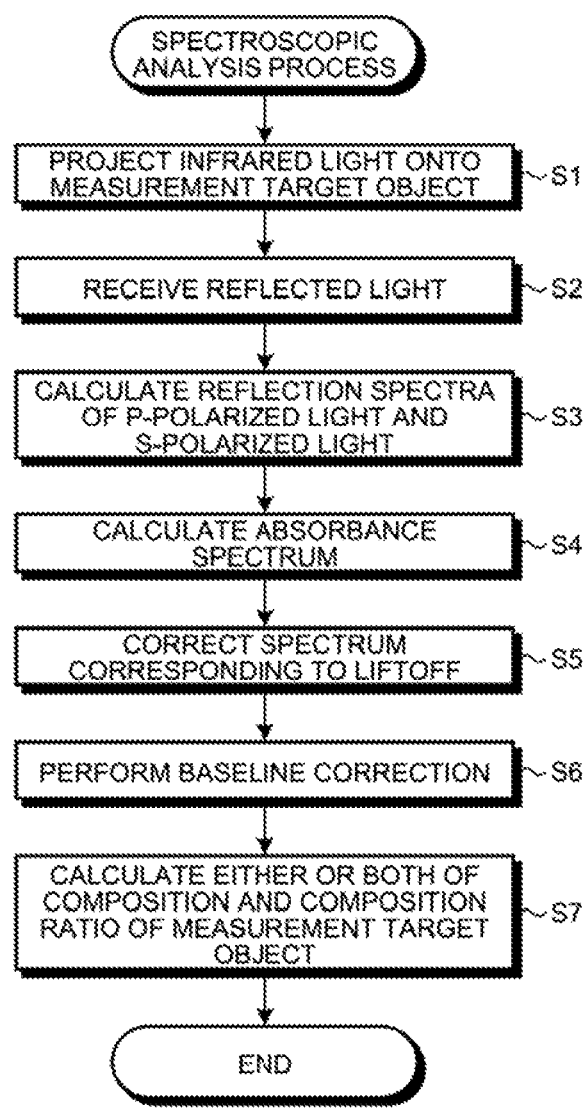
FIG. 7 is a flowchart illustrating the procedure of a spectroscopic analysis process as an embodiment according to aspects of the present invention.

FIG. 7 is a flowchart illustrating the procedure of a spectroscopic analysis process as an embodiment according to aspects of the present invention. The flowchart illustrated in FIG. 7 starts upon having an instruction to execute the spectroscopic analysis process input to the spectroscopic analysis apparatus 1, and the spectroscopic analysis process then proceeds to processing at step S1.

In the processing at step S1, the light projecting unit 2 projects the infrared light IR onto the surface of the measurement target object P at the projection angle α. The processing at step S1 is thereby completed, and the spectroscopic analysis process proceeds to processing at step S2.

In the processing at step S2, the light receiving unit 3 receives reflected light of the infrared light IR from the measurement target object P, splits the reflected light into s-polarized light and p-polarized light, and supplies the p-polarized light and the s-polarized light to the p-polarized light detecting unit 33 and the s-polarized light detecting unit 34, respectively. The p-polarized light detecting unit 33 detects the interferogram of p-polarized light obtained through the separation by the polarized-light separating unit 32, converts the intensity of the interferogram of p-polarized light into an electric signal, and outputs the electric signal to the output unit 4. The s-polarized light detecting unit 34 detects the interferogram of s-polarized light obtained through the separation by the polarized-light separating unit 32, converts the intensity of the interferogram of s-polarized light into an electric signal, and outputs the electric signal to the output unit 4. The processing at step S2 is thereby completed, and the spectroscopic analysis process proceeds to processing at step S3.

Figure 8:
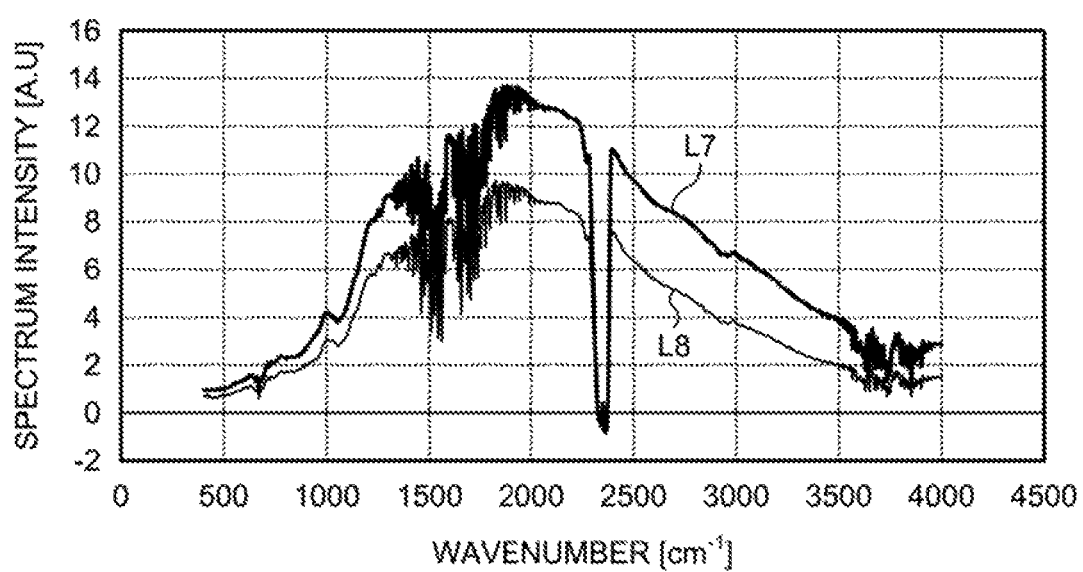
FIG. 8 illustrates an example of measured data of reflection spectra of p-polarized light and s-polarized light.

In the processing at step S3, the output unit 4 applies a Fourier transform to interferograms output from the p-polarized light detecting unit 33 and the s-polarized light detecting unit 34, thereby calculating reflection spectra of the p-polarized light and the s-polarized light. FIG. 8 illustrates an example of measured data of reflection spectra of p-polarized light and s-polarized light. In FIG. 8, a spectrum L7 represents the reflection spectrum of the p-polarized light, and a spectrum L8 represents the reflection spectrum of the s-polarized light. The processing at step S3 is thereby completed, and the spectroscopic analysis process proceeds to processing at step S4.

Figure 9:
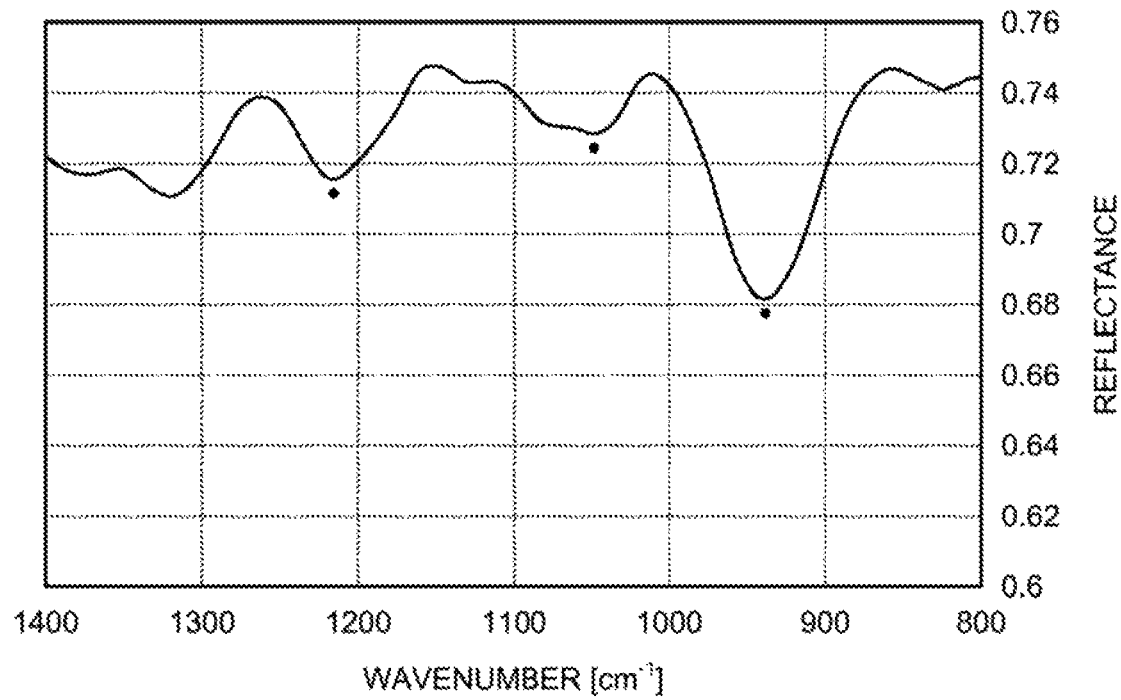
FIG. 9 illustrates reflectance spectra calculated from the reflection spectra illustrated in FIG. 8 of the p-polarized light and the s-polarized light.

In the processing at step S4, the output unit 4 calculates, as a reflectance, the ratio between the intensity of the reflection spectrum of the p-polarized light and the intensity of the reflection spectrum of the s-polarized light in accordance with Equation (1) described above. FIG. 9 illustrates reflectance spectra calculated from the reflection spectra illustrated in FIG. 8 of the p-polarized light and the s-polarized light. As illustrated in FIG. 9, the peaks of main components can be observed in the reflectance spectrum.

Figure 10:
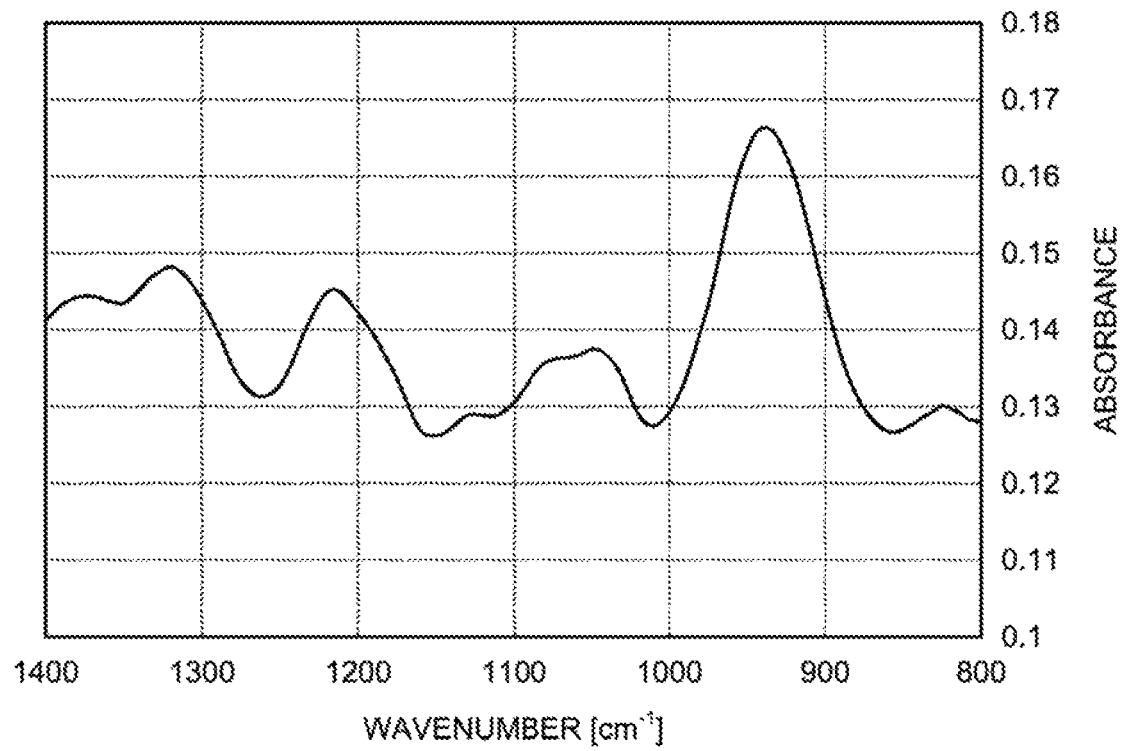
FIG. 10 illustrates an absorbance spectrum calculated from the reflectance spectrum illustrated in FIG. 9.

Subsequently, the output unit 4 converts the reflectance into an absorbance by taking the common logarithm of the reflectance. FIG. 10 illustrates an absorbance spectrum calculated from the reflectance spectrum illustrated in FIG. 9. An absorption spectrum of a coating present on the surface of the measurement target object P can be thereby calculated. The processing at step S4 is thereby completed, and the spectroscopic analysis process proceeds to processing at step S5.

In the processing at step S5, the output unit 4 corrects the absorbance spectra of the p-polarized light and the s-polarized light based on a distance (actual liftoff value) measured between the measurement target object P and the spectroscopic analysis apparatus 1 by the distance measuring device 5. More specifically, as described above, a change in the liftoff reduces the entire light quantity and changes the spectrum in a specific wavelength. While the reduction in the total light intensity is canceled by the calculation of the ratio between the s-polarized light and p-polarized light and baseline correction, the change of the spectrum is not canceled and becomes disturbance. Particularly when a change of the spectrum due to a change in the liftoff overlaps the spectrum of a component of the measurement target object P, measurement is impossible. For this reason, in this processing at step S5, with data previously prepared of absorbance spectra corresponding to liftoff value, the output unit 4 corrects the absorbance spectrum between the p-polarized light and the s-polarized light with reference to data of an absorbance spectrum corresponding to a measured actual liftoff value.

Figure 11:
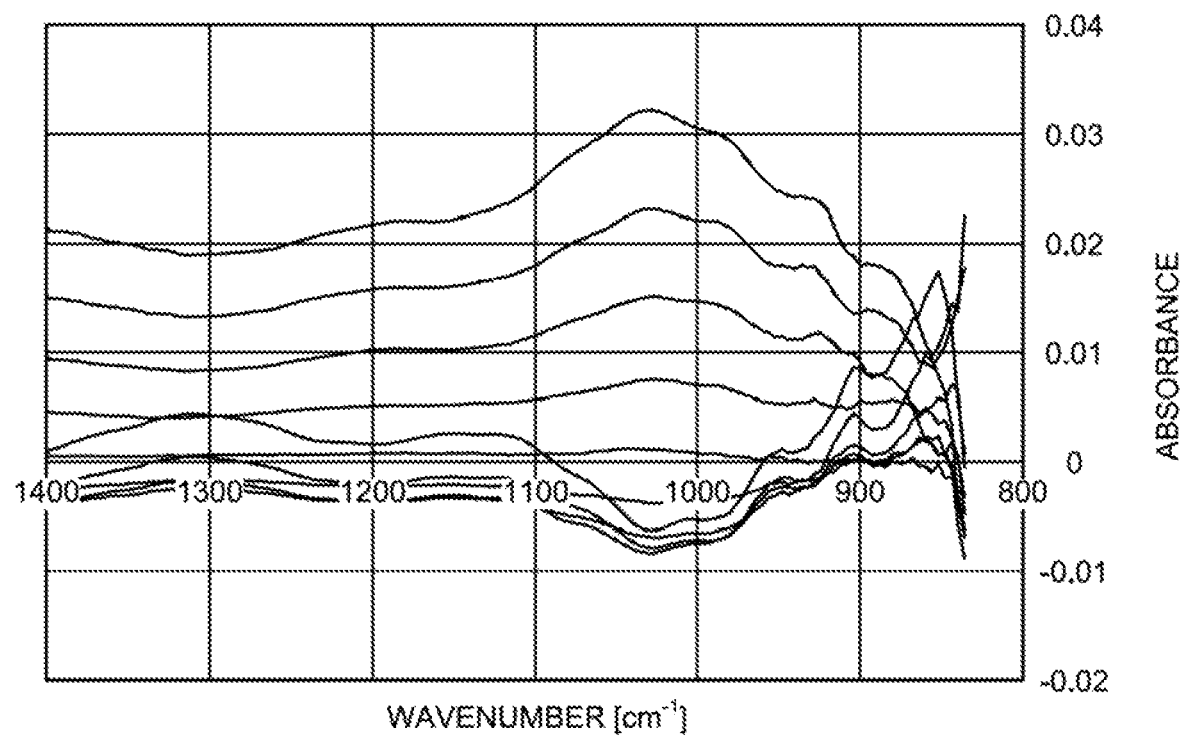
FIG. 11 illustrates an example of changes in absorbance spectrum of s-polarized light that accompany changes in liftoff.
Figure 12:
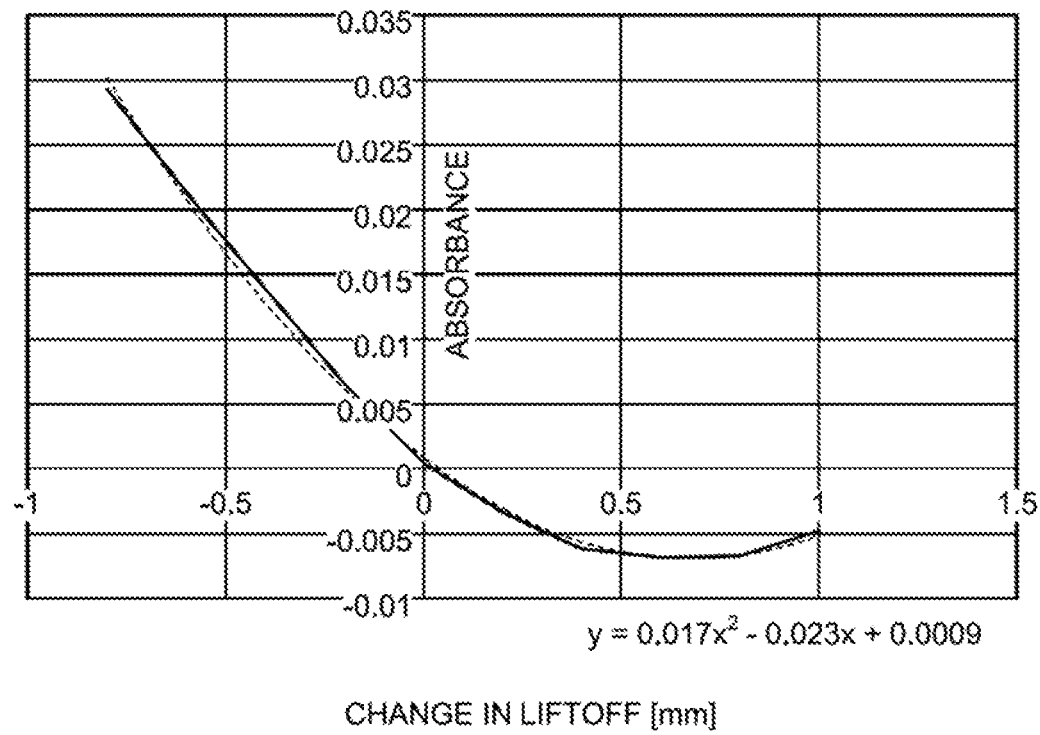
FIG. 12 illustrates an example of changes in absorbance that accompany changes in liftoff.

FIG. 11 illustrates an example of the data of absorbance spectra corresponding to liftoff value. As an example, data of absorbance spectra for a gold mirror when the liftoff value is changed can be used. FIG. 11 illustrates changes of the absorbance spectrum due to s-polarized light when the liftoff is changed from a reference position that centers on focal position within a range of ±1 mm in steps of 0.2 mm. Subsequently, an interpolation formula is established in advance that represents changes in absorbance in association with changes in liftoff value. As an example, changes in absorbance at a wavenumber of 980 $cm^{-1}$ are illustrated in FIG. 12. While it is appropriate to approximate, to a quadratic function, a curve that represents the absorbance in the present example, an applicable approximation formula is not limited thereto. When a measured liftoff is displaced from the reference value, it is considered that changes in the spectra are superimposed. An absorbance corresponding to the amount of a shift of the liftoff is subtracted. Distance correction is performed on actually measured data by applying this operation on the absorbance spectra from the s-polarized light and the p-polarized light.

Figure 13:
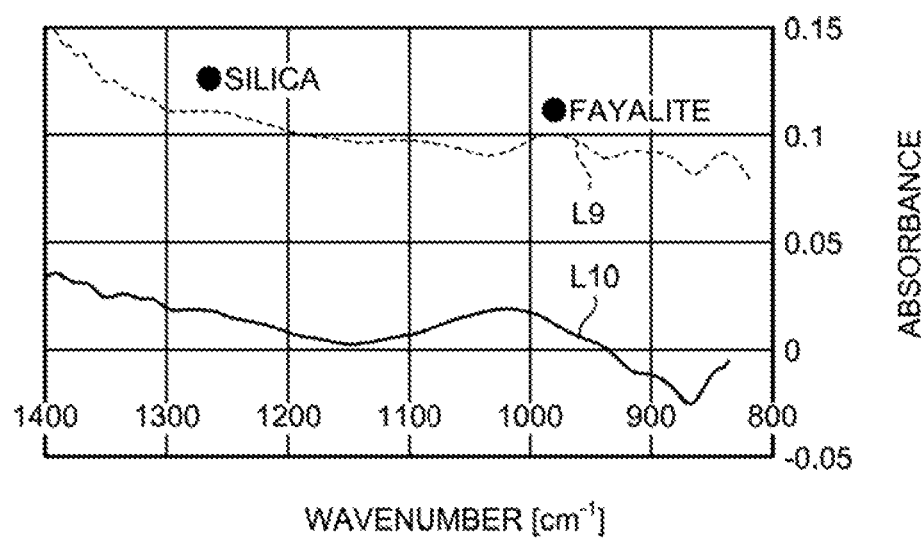
FIG. 13 illustrates the absorbance spectra of p-polarized light and s-polarized light when the focus was missed.

More specifically, FIG. 13 illustrates examples of absorbance spectra of the p-polarized light and the s-polarized light when the focus was missed. In FIG. 13, a broken line L9 represents the absorbance spectrum of the p-polarized light, and a solid line L10 represents the absorbance spectra of the s-polarized light. As illustrated in FIG. 13, peaks can be found at positions corresponding to silica and fayalite in the absorbance spectrum L9 for the p-polarized light. In contrast, a change in the spectrum as described above can be found at around a wavenumber of 1000 $cm^{-1}$ in the absorbance spectrum L10 for s-polarized light. The size of this change in the spectrum is large as compared to a change in the spectrum of the p-polarized light. Consequently, calculation of the intensity ratio between the spectra of the p-polarized light and the s-polarized light in this state covers up a spectrum corresponding to fayalite.

Figure 14:
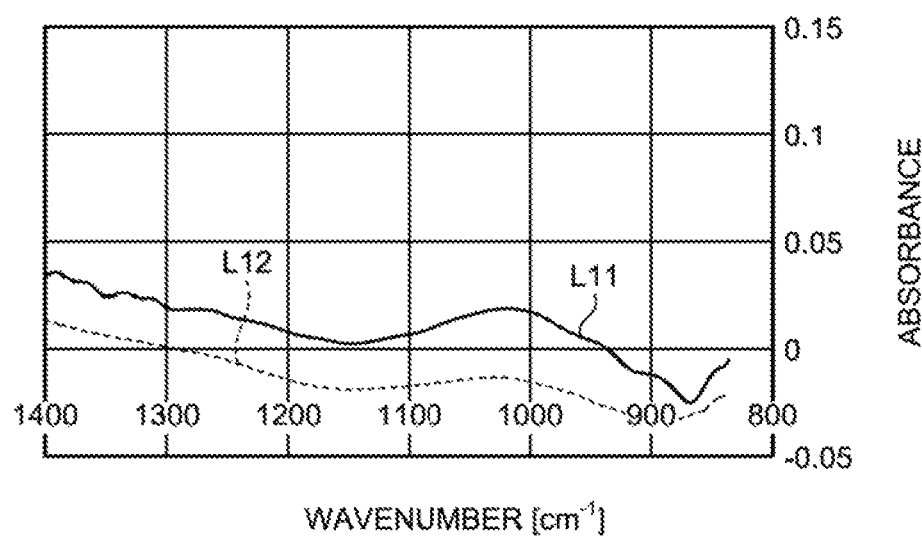
FIG. 14 illustrates the absorbance spectrum of s-polarized light before and after distance correction.

Thus, calculation for correction is performed based on the data illustrated in FIG. 11 and FIG. 12. The liftoff in this example was 0.8 mm off from the reference value, the absorbance spectrum acquired with a gold mirror at 0.8 mm is incorporated in the calculation. An absorbance spectrum obtained as a result for the s-polarized light is illustrated in FIG. 14. A solid line L11 illustrated in FIG. 14 represents an uncorrected absorbance spectrum for the s-polarized light (the same as the one represented by the solid line L10 illustrated in FIG. 13), and a broken line L12 represents a corrected absorbance spectrum for the s-polarized light. As illustrated in FIG. 14, it can be found that the absorbance spectrum was cleared of deformation and was substantially flat. Thus, spectrum correction using actual liftoff value is enabled. As a result, changes in the spectrum due to fluctuations in the liftoff during operation of the apparatus and displacement installation of the apparatus are avoided, which enables stable measurement of a surface composition. The processing at step S5 is thereby completed, and the spectroscopic analysis process proceeds to processing at step S6. This processing at step S5 may be omitted when amounts of fluctuations in the liftoff is within an allowable range.

In the processing at step S6, the output unit 4 performs baseline correction on the absorbance spectrum obtained through the processing at step S5. The baseline correction may be performed in such a manner that any region other than a peak wavelength attributable to a known component in the measurement target object P is set to zero. For example, it is known that a steel sheet that contains silicon (Si) as an element contains components such as fayalite and silica, and the spectra thereof is also known. It can be accordingly found, even from the absorbance spectrum after the distance correction illustrated in FIG. 14 that is yet to undergo the baseline correction, that these components are contained. For a steel material that contains another element, the same principle can be applied to the target element and its oxide, whereby a known spectrum can be found for the baseline correction to be performed.

Figure 15:
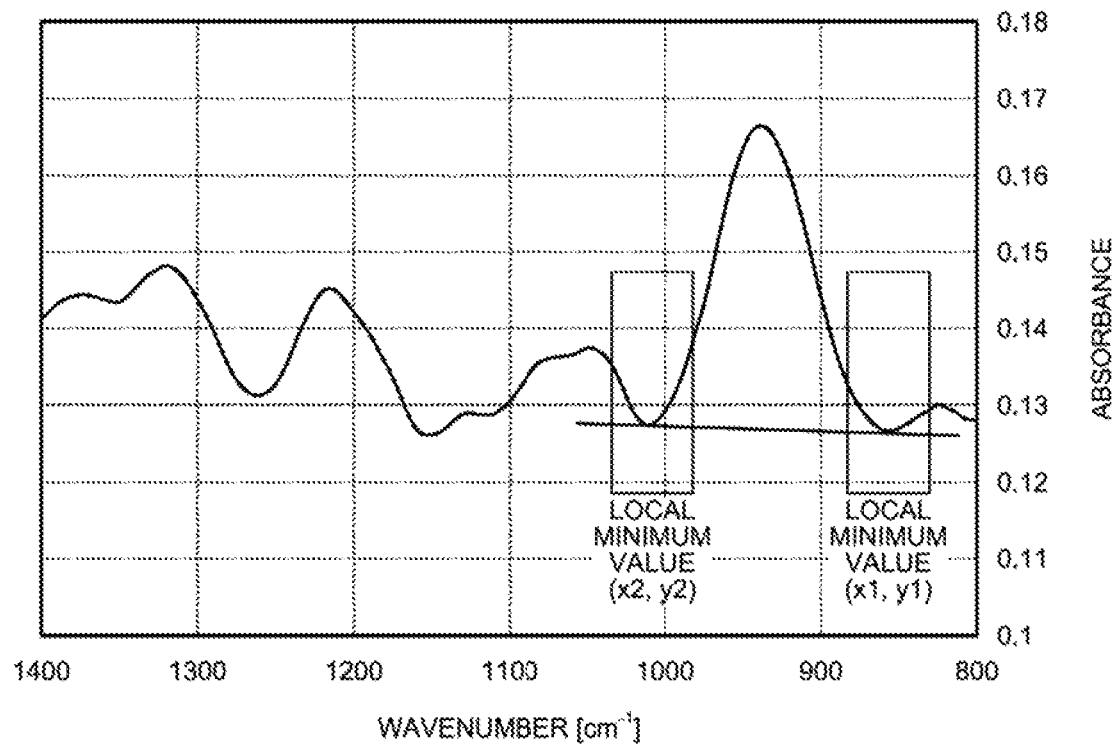
FIG. 15 illustrates a baseline correction method.

However, it can be found that offsets are present depending on the polarization characteristics of the light source as well as of midway parts of the optical system. The output unit 4 carries out the baseline correction accordingly. Specifically, in the present embodiment, the correction is applied in such a manner that a trough between each adjacent peaks is set to zero. More specifically, s-polarized light and p-polarized light are, in principle, supposed to have the same level of absorbance at wavenumbers that do not have sensitivity to infrared light. Therefore, calculation to set a local minimum point at the foot of each peak to zero is carried out in the baseline correction as illustrated in FIG. 15 after it is confirmed that a corresponding absorption spectrum does not present.

Figure 16:
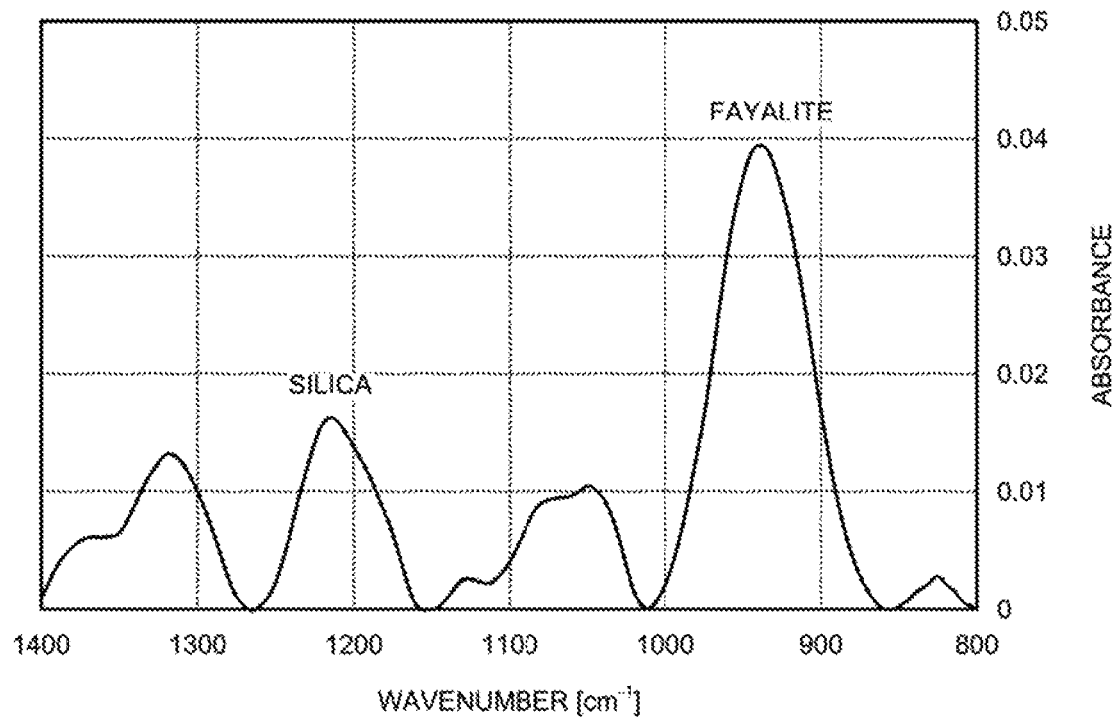
FIG. 16 illustrates a result of baseline correction performed on the absorbance spectrum after distance correction illustrated in FIG. 14.

More specifically, in the first place, search ranges are set between some peaks attributable to a known component, and local minimum values $(x1, y1)$ and $(x2, y2)$ are obtained. When respective absorbances before and after the correction are denoted as $y$ and $Y$, respectively, using each of the local minimum values, a gradient $A$ is expressed using Equation (5) given below. Thereafter, the baseline correction is carried out with the absorbance $Y$ after the correction formulated as Equation (6) given below. The result of the baseline correction performed on four peaks in accordance with this principle is illustrated in FIG. 16. It can be found that peaks attributable to known components were clearly separated. The processing at step S6 is thereby completed, and the spectroscopic analysis process proceeds to processing at step S7.

$$A=(y2-y1)/(x2-x1) \quad (5)$$

$$Y=(y-y1)-A(x-x1) \quad (6)$$

In the processing at step S7, from the absorbance spectrum obtained through the baseline correction, the output unit 4 calculates either or both of the composition and the composition ratio of the surface of the measurement target object using a known method that utilizes peak areas and peak intensities. The composition or the basis weight of oxygen in an oxide film, for example, can be thus calculated. Additionally, makes it possible to watch the composition of the film by calculating the fayalite/silica ratio, or to confirm whether an oxide such as FeO (which is harmful to operation if the amount or the oxygen number exceeds a range for ordinary operation) is not produced. Furthermore, using two or more of the present apparatuses or causing the present apparatus used singly to move in the width direction, makes it possible to evaluate variations in the width direction or to evaluate differences between the front and back sides of strip. The processing at step S7 is thereby completed, and a series of processing formulated as the spectroscopic analysis process ends.

While the embodiments to which the invention made by the inventors of the present invention is applied are described above, the descriptions and drawings that constitute parts of the disclosure of the present invention by way of the present embodiment are not intended to limit the present invention. For example, aspects of the present invention may be applied, as an inspection step included in a steel strip production method, to analysis on either or both of the composition and the composition ratio of the surface of the steel strip. Aspects of the present invention may also be applied to a steel strip quality assurance method to assure the quality of a steel strip by analyzing either or both of the composition and the composition ratio of the surface of the steel strip. Thus, all other embodiments, examples, and operational techniques made by the skilled person or the like based on the present embodiment fall within the scope of the present invention.

INDUSTRIAL APPLICABILITY

According to aspects of the present invention, a spectroscopic analysis apparatus and a spectroscopic analysis method can be provided that enable, even when disturbance is present, either or both of the composition and the composition ratio of the surface of a measurement target object to be analyzed with high accuracy. A steel strip production method can also be provided that enables a steel strip having either or both of a desired surface composition and a desired surface composition ratio to be produced with a high yield. A steel strip quality assurance method can also be provided that enables a high-quality steel strip to be provided.

REFERENCE SIGNS LIST

1 SPECTROSCOPIC ANALYSIS APPARATUS
2 LIGHT PROJECTING UNIT
3 LIGHT RECEIVING UNIT
4 OUTPUT UNIT
5 DISTANCE MEASURING DEVICE
21 FTIR UNIT
21a LIGHT SOURCE
21b INTERFEROMETER
22, 31 OBJECTIVE MIRROR
32 POLARIZED-LIGHT SEPARATING UNIT
33 P-POLARIZED LIGHT DETECTOR

34 S-POLARIZED LIGHT DETECTOR
IR INFRARED LIGHT
P MEASUREMENT TARGET OBJECT

The invention claimed is:

1. A spectroscopic analysis apparatus comprising: a light projecting device configured to project infrared light to a measurement target object; a light receiving device configured to receive, as reflected light, the infrared light reflected by a surface of the measurement target object; and an output device configured to calculate either or both of a composition and a composition ratio of the surface of the measurement target object using the reflected light received by the light receiving device, wherein the light receiving device includes: a separator configured to separate the reflected light into s-polarized light and p-polarized light; a first detector for s-polarized light configured to detect s-polarized light obtained through the separation by the separator and output an electric signal indicating an intensity of the s-polarized light to the output device; and a second detector for p-polarized light configured to detect p-polarized light obtained through the separation by the separator and output an electric signal indicating an intensity of the p-polarized light to the output device; and the output device is configured to: calculate an absorbance based on a ratio between the intensities of the s-polarized light and the p-polarized light using the electric signals output from the detector for s-polarized light and the detector for p-polarized light; and calculate either or both of the composition and the composition ratio of the surface of the measurement target object using an intensity of the absorbance at any desired wavenumber.

2. The spectroscopic analysis apparatus according to claim 1, further comprising a distance measuring device configured to measure a distance between a position irradiated with the infrared light on the measurement target object and a spectroscopic measurement apparatus, wherein
the output device corrects the absorbance in accordance with values measured by the distance measuring device.

3. A spectroscopic analysis method, comprising: projecting infrared light to a measurement target object; receiving, as reflected light, the infrared light reflected by a surface of the measurement target object; and calculating either or both of a composition and a composition ratio of the surface of the measurement target object using the reflected light received at the receiving, wherein the receiving includes: separating the reflected light into s-polarized light and p-polarized light; first detecting s-polarized light obtained through the separating, and outputting an electric signal that indicates an intensity of the detected s-polarized light; and second detecting p-polarized light obtained through the separating, and outputting an electric signal that indicates an intensity of the detected p-polarized light, the first detecting and the second detecting being performed in any order; and the calculating includes: calculating an absorbance based on a ratio between the intensities of the s-polarized light and the p-polarized light using the electric signals output at the detecting s-polarized light and at the detecting p-polarized light; and calculating either or both of the composition and the composition ratio of the surface of the measurement target object using an intensity of the absorbance at any desired wavenumber.

4. A steel strip production method, comprising:
producing a steel strip; and
analyzing either or both of a composition and a composition ratio of a surface of the steel strip produced at the producing using the spectroscopic analysis method according to claim 3.

5. A method of assuring steel strip quality, comprising:
analyzing either or both of a composition and a composition ratio of a surface of a steel strip using the spectroscopic analysis method according to claim 3; and
conducting quality assurance of the steel strip based on an analysis result obtained at the analyzing.

* * * * *